United States Patent [19]
Isaacson

[11] Patent Number: 6,056,726
[45] Date of Patent: *May 2, 2000

[54] SELF-CONTAINED SAFETY INTRAVENOUS CATHETER INSERTION DEVICE

[76] Inventor: Dennis Ray Isaacson, 3684 W. 4625 South, Roy, Utah 84067

[*] Notice: This patent issued on a continued prosecution application filed under 37 CFR 1.53(d), and is subject to the twenty year patent term provisions of 35 U.S.C. 154(a)(2).

[21] Appl. No.: 08/395,615

[22] Filed: Feb. 28, 1995

Related U.S. Application Data

[63] Continuation-in-part of application No. 08/315,880, Sep. 30, 1994, Pat. No. 5,573,510, and a continuation-in-part of application No. 08/202,729, Feb. 28, 1994, abandoned.

[51] Int. Cl.[7] ................................. A61M 5/178
[52] U.S. Cl. .................. 604/164; 604/198; 604/195
[58] Field of Search .................. 604/162, 163, 604/164, 187, 198, 195, 161, 165

[56] References Cited

U.S. PATENT DOCUMENTS

| | | | |
|---|---|---|---|
| 4,160,450 | 7/1979 | Doherty | 178/214.4 |
| 4,316,463 | 2/1982 | Schmitz et al. | 128/218 F |
| 4,542,749 | 9/1985 | Caselgrandi et al. | 128/752 |
| 4,747,831 | 5/1988 | Kulli | 604/110 |
| 4,747,836 | 5/1988 | Luther | 604/198 |
| 4,838,869 | 6/1989 | Allard | 604/195 |
| 4,838,871 | 6/1989 | Luther | 604/192 |
| 4,850,968 | 7/1989 | Romano | 604/110 |

(List continued on next page.)

*Primary Examiner*—Corrine McDermott
*Assistant Examiner*—Cris L. Rodriguez
*Attorney, Agent, or Firm*—Workman, Nydegger & Seeley

[57] ABSTRACT

The present invention relates to intravenous catheter insertion devices which employ a sharp needle to introduce and emplace an intravenous catheter into a body vessel of a patient. The sharp needle end is positioned to extend from within the catheter such that the needle and catheter can be introduced into the body vessel which is pierced by the sharp needle. Following use of the present intravenous catheter insertion device to introduce and emplace an intravenous catheter into a patient's body vessel, the needle is withdrawn from within the catheter and the device is separated from the catheter such that only the catheter remains within the body vessel. The safety intravenous catheter insertion device of the present invention comprises self-contained coupling means for preventing separation of the catheter from the device until the needle is substantially transposed into a safety receptacle to thereby permit the used needle to be safely handled and discarded. It is preferred to provide a self-contained safety intravenous catheter insertion device having automatic needle transposal means and it is especially preferred to have automatic transposal means triggered by manipulations related to catheter placement, i.e., positioning of the catheter at a selected position relative to the needle. The selected relative catheter position is preferably when the entire catheter is positioned just beyond or nearly beyond the needle point. In this manner, transposition of the needle into the safety receptacle occurs automatically when the catheter is placed in the selected position, and placement of the catheter in the selected position occurs during withdrawal of the needle from within the emplaced catheter thereby permitting the needle to remain within the catheter during emplacement to thereby facilitate guiding and maneuvering of the catheter to the desired emplacement position.

11 Claims, 5 Drawing Sheets

U.S. PATENT DOCUMENTS

| | | | |
|---|---|---|---|
| 4,874,382 | 10/1989 | Lindemann et al. | 604/195 |
| 4,887,998 | 12/1989 | Martin et al. | 604/110 |
| 4,894,055 | 1/1990 | Sudnak | 604/198 |
| 4,900,307 | 2/1990 | Kulli | 604/110 |
| 4,904,242 | 2/1990 | Kulli | 604/110 |
| 4,927,414 | 5/1990 | Kulli | 604/110 |
| 4,936,830 | 6/1990 | Verlier | 604/110 |
| 4,941,883 | 7/1990 | Venturini | 604/186 |
| 4,966,593 | 10/1990 | Lennox | 604/198 |
| 4,973,316 | 11/1990 | Dysarz | 604/195 |
| 4,978,343 | 12/1990 | Dysarz et al. | 604/195 |
| 4,994,034 | 2/1991 | Botich et al. | 604/110 |
| 5,000,740 | 3/1991 | Ducharme et al. | 604/162 |
| 5,013,301 | 5/1991 | Marotta, Jr. et al. | 604/197 |
| 5,017,187 | 5/1991 | Sullivan | 604/110 |
| 5,019,044 | 5/1991 | Tsao | 604/110 |
| 5,049,133 | 9/1991 | Villen Pascual | 604/110 |
| 5,053,010 | 10/1991 | McGary et al. | 604/110 |
| 5,053,014 | 10/1991 | Van Heugten | 604/167 |
| 5,064,419 | 11/1991 | Gaarde | 604/195 |
| 5,069,667 | 12/1991 | Freundlich et al. | 604/110 |
| 5,085,640 | 2/1992 | Gibbs | 604/110 |
| 5,088,986 | 2/1992 | Nusbaum | 604/195 |
| 5,092,853 | 3/1992 | Covetier, II | 604/195 |
| 5,102,394 | 4/1992 | Lasaitis et al. | 604/164 |
| 5,112,307 | 5/1992 | Haber et al. | 604/110 |
| 5,114,404 | 5/1992 | Paxton et al. | 604/110 |
| 5,114,410 | 5/1992 | Caralt Battle | 604/195 |
| 5,120,308 | 6/1992 | Hess | 604/95 |
| 5,120,310 | 6/1992 | Shaw | 604/110 |
| 5,122,118 | 6/1992 | Haber et al. | 604/110 |
| 5,125,414 | 6/1992 | Dysarz | 128/763 |
| 5,129,884 | 7/1992 | Dysarz | 604/164 |
| 5,147,303 | 9/1992 | Martin | 604/110 |
| 5,163,918 | 11/1992 | Righi et al. | 604/198 |
| 5,167,641 | 12/1992 | Schmitz | 604/196 |
| 5,176,650 | 1/1993 | Haining | 604/164 |
| 5,180,369 | 1/1993 | Dysarz | 604/110 |
| 5,180,370 | 1/1993 | Gillespie | 604/110 |
| 5,186,712 | 2/1993 | Kelso et al. | 604/165 |
| 5,188,599 | 2/1993 | Boich et al. | 604/110 |
| 5,188,613 | 2/1993 | Shaw | 604/195 |
| 5,190,526 | 3/1993 | Murray et al. | 604/110 |
| 5,215,525 | 6/1993 | Sturman | 604/164 |
| 5,273,540 | 12/1993 | Luther et al. | 604/110 |
| 5,312,359 | 5/1994 | Wallace | 604/164 |
| 5,376,075 | 12/1994 | Haughton et al. | 604/158 |
| 5,382,237 | 1/1995 | Dauherty | 604/164 |
| 5,411,486 | 5/1995 | Zadini et al. | 604/198 |

SELF-CONTAINED SAFETY INTRAVENOUS CATHETER INSERTION DEVICE

RELATED APPLICATIONS

This application is a continuation-in-part of copending application Ser. No. 08/315,880 filed Sep. 30, 1994, now U.S. Pat. No. 5,573,510 incorporated herein by reference, a continuation-in-part of application Ser. No. 08/202,729 filed Feb. 28, 1994, now abandoned.

BACKGROUND OF THE INVENTION

1. The Field of the Invention

The present invention relates to intravenous catheter insertion devices which employ a sharp needle to introduce and emplace an intravenous catheter into a body vessel of a patient. More particularly, the present invention relates to intravenous catheter insertion devices having protective needle transposal means for transposing a used needle into a safety receptacle and having self-contained coupling means for preventing separation of the catheter from the device until such time as the needle has been transposed into the safety receptacle.

2. The Relevant Technology

The introduction and emplacement of intravenous catheters into a body vessel of a patient by trained medical personnel is a common procedure utilizing fairly standardized apparatus and methods. Although the procedure for intravenous catheter insertion is fairly simple, medical practitioners must learn, develop, and maintain good technique which accomplishes the procedure quickly and comfortably for the patient as well as safely for both the patient and the practitioner. Intravenous catheter insertion devices typically employ a sharp needle to introduce and emplace an intravenous catheter into a body vessel of a patient. The needle is positioned within the catheter and the sharp needle end extends beyond the catheter such that the needle and catheter can be introduced nearly concomitantly into the body vessel immediately after the vessel has been pierced by the sharp needle end. It is usually desirable to retain the needle within the catheter to some extent to facilitate guiding and maneuvering of the catheter to a desired emplacement position within the body vessel. Often, the catheter is rotated into position around the needle and moved forward and backward along the needle during these maneuverings. Once the intravenous catheter is satisfactorily positioned within the vessel, the needle is typically withdrawn from inside the catheter leaving the catheter within the body vessel.

It will be appreciated that the needle used to introduce and emplace the catheter has contacted the patient's blood and other body fluids. It is well-known that an accidental needle stick with a used needle or any reuse of a used needle may result in transmission of harmful contaminants or infectious diseases including diseases such as AIDS or hepatitis. Because of this threat, any used needle should be carefully handled and discarded in a manner that minimizes this risk.

Because of the safety concerns related to needle use, numerous safety devices for handling needles, including retractable needles and extendable sheaths of various types, have been developed. For example, U.S. Pat. No. 4,160,450 issued on Jul. 10, 1979 to Doherty, disclosed a housing to hold the needle following use. The housing is formed as a liquid flow chamber connected to the catheter. A patent issued to Lasaitis et al. on Apr. 7, 1992, U.S. Pat. No. 5,102,394, disclosed a catheter assembly having a needle attached to a tab member which could be moved to retract the needle into a protective shield member. A similar device is taught in U.S. Pat. No. 5,176,650, issued to Haining on Jan. 5, 1993. The Haining device, however, also includes means for locking the needle in both the extended and the retracted positions.

U.S. Pat., No. 4,747,831, issued to Kulli on May 31, 1988, taught an intravenous catheter insertion device having a spring-loaded needle-carrying block that retracts into a handle when a manually-releasable latch is triggered. U.S. Pat. No. 4,973,316 issued to Dysarz on Nov. 27, 1990, disclosed a spring-loaded piston for retracting a needle into the barrel of a syringe when a trigger element is disengaged from the piston. Two subsequent patents issued to Dysarz, U.S. Pat. No. 5,125,414 issued Jun. 30, 1992 and U.S. Pat. No. 5,129,884 issued Jul. 14, 1992. Both patents disclosed a spring-loaded piston for retracting a needle which is activated by unthreading a latch for use in connection with, respectively, a blood-sampling device and an intravenous catheter insertion device.

Despite the above-described devices and numerous others known in the art, some problems remain. In particular, some of the safety features require cumbersome or two-handed manipulations to activate. Some of the devices do not ensure retention of the needle after activation of the safety feature. The safety feature of some devices can be easily disabled or "reloaded" such that the needle can be reused. Many of the devices can be used to introduce and emplace a catheter whether or not the safety feature is activated thereby making the safety feature optional rather than mandatory.

U.S. Pat. No. 5,092,853 issued Mar. 3, 1992 to Couvertier II and disclosed a spring-loaded retractable needle adapted to be held in the extended position by resiliently biased jaws. The jaws could be released to permit needle retraction either by plunger movement within a syringe barrel or by relative forward movement of a catheter fitted with means to squeeze the jaws. It can be seen, however, that the catheter insertion device of Couvertier II is not a separate and self-contained device for use with conventional catheters but, instead, requires a specially adapted catheter fitted with means to squeeze the jaws and prevent release of the needle. Moreover, this special catheter must be properly attached to prepare the device for use and the special catheter must thereafter remain in the properly attached position until such time as needle retraction is desired. Because only very slight relative forward movement of the catheter will release the jaws and cause needle retraction, it is possible to inadvertently move the catheter slightly and prematurely retract the needle. Such slight relative forward movement and triggering of needle retraction can occur during typical manipulations directed to maneuvering the catheter into a desired emplacement position following introduction of the catheter into the body vessel. If the inadvertent premature needle retraction occurs after the catheter has been introduced into a body vessel but before the catheter has been guided and maneuvered into the desired emplacement position within the body vessel, satisfactory emplacement of the catheter may be hindered or even prevented such that the catheter must be withdrawn and another catheter insertion device obtained and used. Such slight relative forward movement and triggering of needle retraction could also occur even before the catheter has been introduced into the body vessel. If this inadvertent premature needle retraction occurs before the catheter has been introduced into the body vessel, the device must be discarded and a second device obtained. Such inadvertent premature needle retraction causing failure of the device during an urgent medical situation could have serious detrimental consequences.

It would be an advantage to provide a self-contained safety intravenous catheter insertion device which requires transposal of the needle into a safety receptacle prior to separation of the catheter from the device to thereby prevent a user from omitting or circumventing activation of the protective needle transposal means and to inhibit needle misuse by preventing the needle from being separated from the catheter in usable condition. It would be a further advantage to provide such a device wherein the needle is substantially irreversibly retained within the safety receptacle to thereby prevent needle reuse and to permit the safety receptacle and the transposed needle to be safely handled and discarded. It would be an additional advantage to provide an intravenous catheter insertion device having automatic needle transposal means triggered by positioning of the catheter at a selected position relative to the needle wherein such relative position is selected to minimize the possibility of inadvertent premature transposal of the needle into the safety receptacle.

SUMMARY AND OBJECTS OF THE INVENTION

The present invention relates to intravenous catheter insertion devices which employ a sharp needle to introduce and emplace an intravenous catheter into a body vessel of a patient. Once the catheter is emplaced, the needle is typically withdrawn from the body vessel. As used herein, the term intravenous catheter insertion device does not include the intravenous catheter itself. Because the device is used to introduce and emplace a catheter, however, the description of the device must necessarily refer to the catheter in relation to the device. It will be appreciated that the device of the present invention is self-contained and adaptable for use with various catheters.

It is an object of the present invention to provide a self-contained safety intravenous catheter insertion device having coupling means for preventing separation of the catheter from the insertion device until the needle has been transposed into a safety receptacle. The coupling means ensures that the catheter cannot be separated from the insertion device prior to protective transposal of the needle to thereby prevent the needle from being separated from the catheter and misused. This coupling of the act of protective needle transposal to the act of catheter separation also prevents a user from circumventing or omitting activation of the protective needle transposal means because the needle must be transposed before the catheter can be separated from the insertion device. The coupling feature is preferably combined with automatic needle transposal means but it will be appreciated that this feature is also advantageous in devices having manual needle transposal means.

It is a further object to provide an intravenous catheter insertion device which permits transposal of the needle into a disposable safety receptacle such that the needle is substantially irreversibly retained within the safety receptacle. In this manner, the used needle can be safely discarded and reuse of the needle is prevented.

It is another object of the present invention to provide a self-contained safety intravenous catheter insertion device which permits automatic transposal of the needle into a safety receptacle to thereby sheath the needle and prevent further contact with the needle. The transposal of the needle is "automatic" in the sense that transposal is triggered by positioning of the catheter at a selected position relative to the needle rather than by a separate manipulation of the device to effect needle transposal. The selected relative position is preferably when the entire catheter is positioned substantially relatively beyond the needle point as occurs upon withdrawal of the needle from within the emplaced catheter. Because transposition of the needle occurs automatically when the catheter is placed in the selected position, and placement of the catheter in the selected position occurs during withdrawal of the needle from the emplaced catheter, use of the protective needle transposal means cannot be omitted or circumvented by user error. Moreover, because needle transposal does not occur until the entire catheter is positioned substantially relatively beyond the needle point, the needle remains within the catheter to facilitate maneuvering of the catheter to the desired emplacement position. In this manner, inadvertent premature transposal of the needle, i.e., transposal before the catheter has been positioned as desired, is essentially prevented.

These and other objects and features of the present invention will become more fully apparent from the following description and appended claims, or may be learned by the practice of the invention as set forth hereinafter.

To achieve the foregoing objects, and in accordance with the invention as embodied and broadly described herein, a preferred embodiment of the present invention comprises a needle and a safety receptacle adapted to slidably receive and substantially enclose the needle. The needle is initially retained in a position where a forward needle portion extends from the safety receptacle and a rearward needle portion is secured within the safety receptacle.

In order to effect the desired coupling of the act of needle transposition and the act of catheter separation, the self-contained coupling means of the present invention comprises a catheter holding member and an attached receptacle holding member. The rearward end of the receptacle holding member and the rearward needle portion are slidably engaged with each other within the safety receptacle. The catheter holding member comprises means for releasably securing the catheter to the catheter insertion device. A needle bore is formed within catheter holding member to permit sliding passage of the needle therethrough. It will be appreciated that, because the needle extends through the needle bore in the catheter holding member and the rearward needle portion is secured within the safety receptacle, the needle within the needle bore blocks separation of the catheter from the catheter holding member until such time as the needle has been substantially transposed into the safety receptacle.

It is preferred to provide a self-contained safety intravenous catheter insertion device having automatic needle transposal means. The automatic needle transposal means comprises needle stop means for retaining the needle in a first position where the forward needle portion extends from the safety receptacle and resilient bias means for urging the needle into the safety receptacle and for thereafter retaining the needle within the safety receptacle.

BRIEF DESCRIPTION OF THE DRAWINGS

In order that the manner in which the above-recited and other advantages and objects of the invention are obtained, a more particular description of the invention briefly described above will be rendered by reference to specific embodiments thereof illustrated in the appended drawings. Understanding that these drawings depict specific embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The present invention relates to intravenous catheter insertion devices which employ a sharp needle to introduce and emplace an intravenous catheter into a body vessel of a patient. The sharp needle end is positioned to extend from within the catheter such that the needle and catheter can be introduced into the body vessel which is pierced by the sharp needle. Following emplacement of the intravenous catheter within the vessel, the needle is typically withdrawn from the body vessel. As the needle has contacted the patient's blood and other body fluids, it is desirable to be able to sheath the needle to prevent further contact with the used needle and thereby avoid exposure to those fluids by others.

As used herein, the term intravenous catheter insertion device does not include the intravenous catheter itself. Because the device is to be used to introduce and emplace a catheter, however, the description and illustration of the device must necessarily refer to a catheter in relation to the device. It will be appreciated that the device of the present invention is self-contained in that the device is entirely separable from the catheter and the device can be adapted for use with various conventional catheters or with specially-adapted catheters. Following use of the present intravenous catheter insertion device to introduce and emplace an intravenous catheter into a patent's body vessel, only the catheter itself remains within the body vessel.

Various needle retracting and/or sheathing devices are known in the art. Nevertheless, it would be an advantage to provide a self-contained safety intravenous catheter insertion device which requires transposal of the needle into a safety receptacle prior to separation of the catheter from the device to thereby prevent a user from omitting or circumventing activation of the protective needle transposal means. Such a device, comprising self-contained coupling means for preventing separation of the catheter from the device until needle transposal into a safety receptacle has occurred, is disclosed herein. Once the needle of the self-contained safety intravenous catheter insertion device of the present invention is transposed into the safety receptacle, the needle is substantially irreversibly retained within the safety receptacle to thereby prevent needle reuse. Accordingly, following separation of the catheter from the present device, the safety receptacle and the transposed needle can be safely handled and discarded with minimal risk of harm. Moreover, because the catheter cannot be separated from a non-transposed needle, the coupling means prevents the needle from being separated from the catheter in usable condition to thereby prevent needle misuse.

Figure 1:
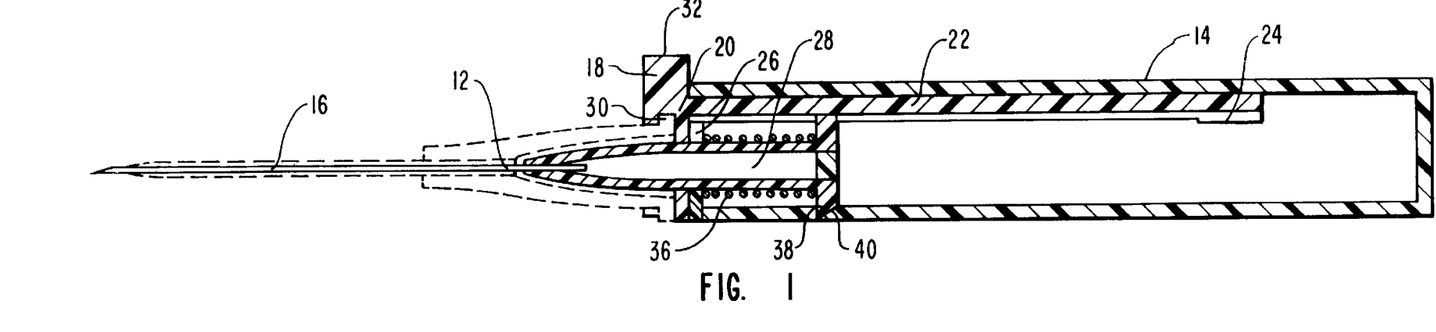
FIG. 1 is a schematic longitudinal cross-section view of a preferred embodiment of the safety intravenous catheter insertion device of the present invention.

An illustrative preferred embodiment of the present invention is shown schematically in longitudinal cross-section in FIG. 1. As shown, catheter insertion device comprises a needle 12 and a safety receptacle 14. The catheter insertion device is preferably molded in customary fashion from plastic material such as polyethylene. The safety receptacle is preferably adapted to slidably receive and substantially enclose the needle. The needle is initially retained in a position where a forward needle portion 16 extends from the safety receptacle 14. A rearward needle portion 28 is secured within the safety receptacle. Typically, a needle for introducing an intravenous catheter is hollow and formed with a flash chamber portion within the rearward needle portion to permit the user to visualize blood entry into the needle and verify proper placement of the needle within a blood vessel. For this reason, the safety receptacle is preferably molded from a transparent plastic material.

In order to effect the desired coupling of the act of needle transposition and the act of catheter separation, the self-contained coupling means of the present invention comprises a catheter holding member 18 and an attached receptacle holding member 20. As shown, a rearward end 22 of receptacle holding member 20 is preferably secured within the safety receptacle 14. The rearward end of the receptacle holding member and the rearward needle portion are slidably engaged with each other within the safety receptacle. As seen in FIG. 1, the receptacle holding member partially encircles the rearward needle portion within the safety receptacle. It will be appreciated that the receptacle holding member could alternatively be configured to substantially fully encircle the rearward needle portion.

The receptacle holding member can be formed from opaque or transparent plastic. If the receptacle holding member is positioned over a flash chamber on the rearward needle portion, however, the receptacle holding member should be formed of transparent material or with a transparent window portion to permit visualization of the flash chamber. Similarly, if a flash chamber is positioned such that the catheter would obstruct visualization, the catheter should also have a transparent portion.

Preferably, the catheter insertion device comprises retention means for ensuring that the receptacle holding member does not detach from the safety receptacle. Various conventional retention means could be used. An example of such retention means is seen in FIG. 1 where the rearward end of the receptacle holding member has an extension 24 which will be retained by a shelf 26 formed in the face of the safety receptacle.

The catheter holding member 18 comprises means for releasably securing the catheter to the catheter insertion device. Typically, the rearward catheter portion is widened and adapted for attachment of tubing. The widened rearward catheter portion forms a hub member which can be secured to the catheter holding member. Such means are known in the art and include various types of lip, groove, or slot configurations adapted to slidingly receive and fittingly engage the rearward portion of an intravenous catheter, shown in dotted line, in a convenient and easily reversed manner. Accordingly, the means for releasably securing the catheter to the catheter insertion device in the preferred embodiment shown in FIG. 1 is a slot 30 formed within catheter holding member 18.

Figure 2:
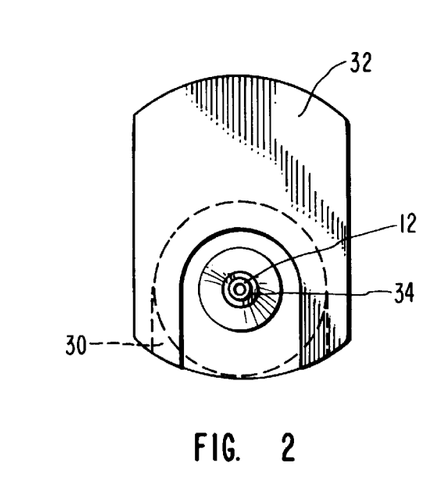
FIG. 2 is a cross-section of the catheter holding member of the preferred embodiment taken along line 2—2 of FIG. 1.

FIG. 2 shows the catheter holding member in schematic cross-section taken along line 2—2 of FIG. 1. As seen in FIG. 2, a needle bore 34 is formed within the catheter holding member to permit sliding passage of the needle 12 therethrough. The rearward portion of the catheter, shown in dotted lines, is slidably received within slot 30. In FIGS. 1 and 2, the catheter holding member is shown with an optional extending tab member 32 to facilitate gripping of the catheter holding member and, if desired, to facilitate moving of the catheter holding member as described below in connection with FIGS. 3 through 6.

It will be appreciated that, because the needle extends through the needle bore in the catheter holding member and the rearward needle portion is secured within the safety receptacle, the needle within the needle bore blocks separation of the catheter from the catheter holding member until such time as the needle has been substantially transposed into the safety receptacle.

It is preferred to provide a self-contained safety intravenous catheter insertion device having automatic needle transposal means. In particular, the preferred needle transposal means are "automatic" in the sense that transposal is triggered by manipulations related to catheter placement, i.e., positioning of the catheter at a selected position relative to the needle, rather than by separate manipulation of the device to effect needle transposal. The selected relative catheter position is preferably when the entire catheter is positioned just beyond or nearly beyond the needle point and is described herein as "substantially relatively beyond" the needle. As it is typically desired to withdraw the needle from the emplaced catheter, it will be appreciated that positioning of the catheter at the selected relative position such that the entire catheter is positioned just beyond or nearly beyond the needle point will necessarily occur during the process of withdrawing the needle from within the emplaced catheter. Because transposition of the needle into the safety receptacle occurs automatically when the catheter is placed in the selected position, and placement of the catheter in the selected position occurs during withdrawal of the needle from within the emplaced catheter, activation of the protective needle transposal means cannot be omitted or circumvented by user error.

Moreover, selection of the relative position of the catheter which triggers automatic needle transposal at the position where the entire catheter is just beyond or nearly beyond the needle point, i.e., substantially relatively beyond the needle, permits the needle to remain within the catheter during emplacement to thereby facilitate guiding and maneuvering of the catheter to the desired emplacement position. In particular, the catheter can be rotated about the needle and moved forward and back along substantially the entire length of the forward needle portion without triggering needle transposal. Accordingly, the needle need not be withdrawn to the position where the entire catheter is positioned substantially relatively beyond the needle such that needle transposal is triggered until such time as the desired catheter emplacement position is achieved. In this manner, inadvertent premature transposal of the needle, i.e., transposal before the catheter has been emplaced in the desired position, is essentially prevented.

Returning to FIG. 1, a presently preferred automatic needle transposal means is illustrated. The automatic needle transposal means comprises needle stop means for retaining the needle in a first position where the forward needle portion 16 extends from the safety receptacle 14 and resilient bias means for urging the needle 12 into the safety receptacle and for thereafter retaining the needle within the safety receptacle. As shown, the resilient bias means preferably comprises a spring 36 surrounding a portion of the needle within the safety receptacle 14. The needle stop means preferably comprises a latch member 38 extending from the rearward needle portion 28 and engaged with a latch notch 40 formed within the side of the safety receptacle 14. The latch member 38 is biased into the latch notch 40 because of the sloping configuration and the pressure from contact between the receptacle holding member 20 positioned within the safety receptacle and the rearward needle portion 28. Accordingly, the needle stop means, i.e., the latch member engaged with the latch notch, are maintained by contact pressure from the receptacle holding member. It will be appreciated that relative movement of the receptacle holding member a predetermined distance with respect to the rearward needle portion, which corresponds to movement of the catheter to the selected position as described above wherein the entire catheter is positioned substantially relatively forward of the needle, will release the contact pressure maintaining the needle stop means.

Figure 3:
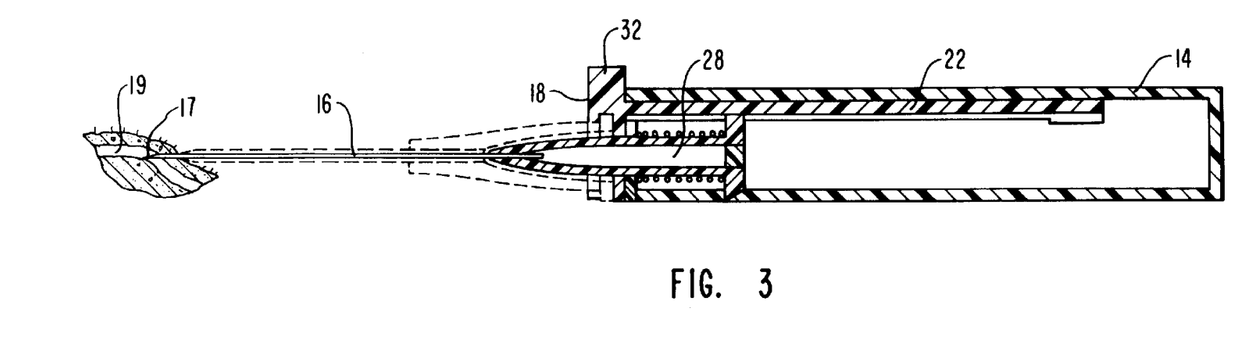
FIG. 3 is a schematic longitudinal cross-section view of the preferred embodiment of FIG. 1 shown during an initial venipuncture.
Figure 4:
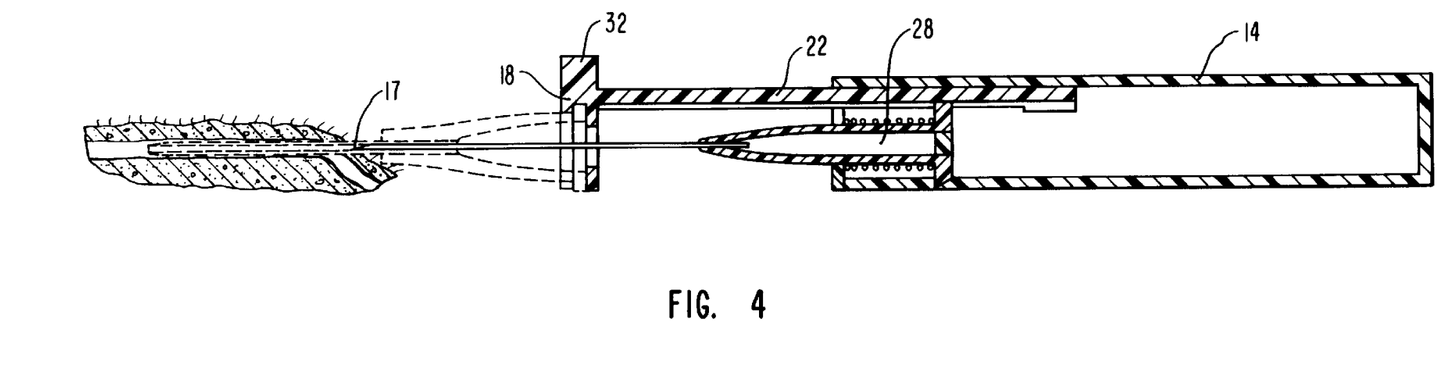
FIG. 4 is the device of FIG. 3 shown during emplacement of a catheter.

FIGS. 3–6 illustrate operation of the coupling means and automatic needle retraction means with respect to the preferred embodiment of FIG. 1. FIG. 3 illustrates the device being used to introduce an intravenous catheter into a body vessel. The forward needle portion 16 has a venipuncturing tip 17 shown entered into a vein 19. FIG. 4 illustrates relative forward movement of the catheter holding member 18 from an initial position adjacent to safety receptacle 14 to an extended position separated from the safety receptacle.

It will be appreciated that movement of the catheter holding member moves the catheter relatively forward of the venipuncturing tip in the vein. The relative forward movement of the catheter holding member can be effected by pushing the catheter holding member forwardly from the safety receptacle. This movement may be facilitated by the extending tab member 32. Alternatively, or in addition, the relative forward movement of the catheter holding member can be effected by holding onto, or pressing against, the catheter and pulling the safety receptacle backwardly from the catheter. The degree of relative forward movement of the catheter can be manually controlled such that a portion of the needle remains within the catheter while the catheter is maneuvered into a desired emplacement position within the vein as seen in FIG. 4.

Figure 5:
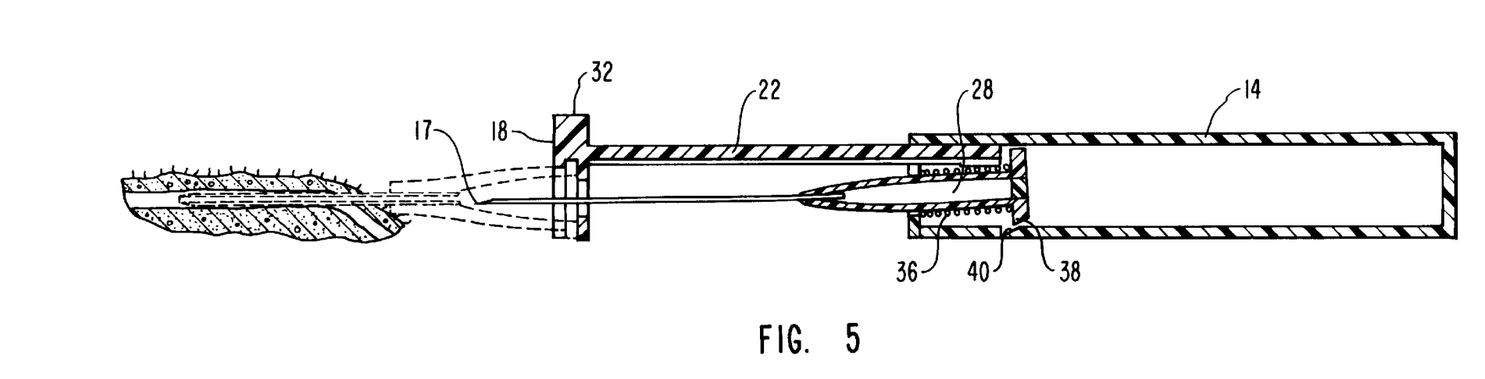
FIG. 5 is the device of FIG. 3 shown at the instant just prior to automatic transposal of the needle into the safety receptacle.

It will further be appreciated that movement of the catheter holding member away from the safety receptacle causes the attached receptacle holding member to slide within the safety receptacle 14 relatively forward with respect to the rearward needle portion 28. Once the desired catheter emplacement position is achieved, the needle can be withdrawn from inside the catheter. This can be achieved either by forwardly advancing the catheter entirely beyond the needle or by backwardly withdrawing the needle from the catheter. In either case, at the point where the entire catheter is positioned just beyond or nearly beyond the needle, the receptacle holding member will have moved, within the safety receptacle, relatively forward with respect to the rearward needle portion to a point which results in release of the contact pressure between the receptacle holding member and the rearward needle portion. This point is illustrated in FIG. 5.

Figure 6:
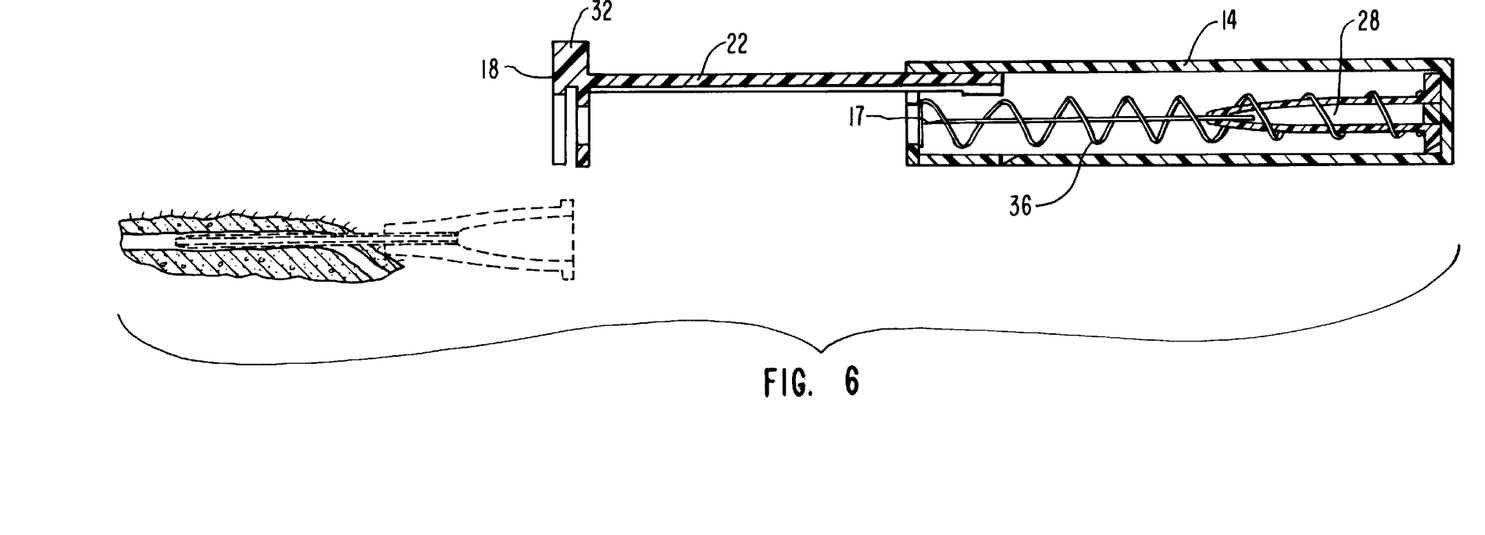
FIG. 6 illustrates the device of FIG. 3 following automatic transposal of the needle into the safety receptacle when the catheter can be separated from the device.

It will be appreciated that release of the contact pressure will cause latch member 38 to disengage from latch notch 40 under the bias force of spring 36. Accordingly, as shown in FIG. 6, the needle becomes transposed to within the safety receptacle and is retained in the transposed position under the bias force of spring 36. Also as seen in FIG. 6, once the needle is no longer blocking separation of the catheter from the catheter holding member 18, the emplaced catheter can be separated from the device. The separated device, containing the used needle, can be safely handled and discarded to thereby prevent exposure to, or reuse of, the used needle.

Figure 7:
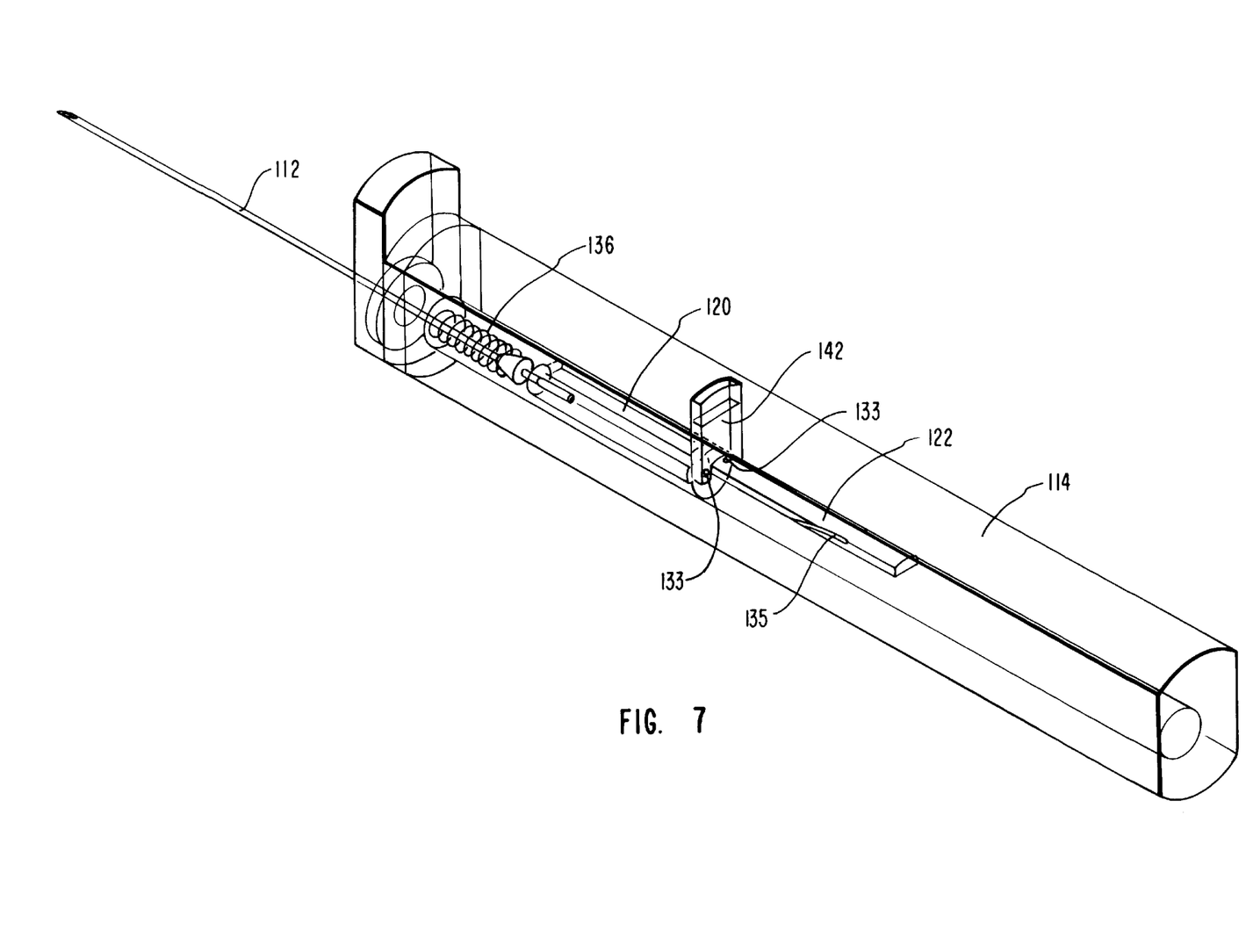
FIG. 7 is a perspective schematic view of a second preferred embodiment of the safety intravenous catheter insertion device of the present invention.

It will be appreciated that automatic needle transposal means may be embodied in other forms. The preferred embodiments illustrated herein are intended to be exemplary only and not restrictive. FIG. 7 depicts a perspective view of a second preferred embodiment of the safety intravenous catheter insertion device of the present invention having self-contained coupling means and automatic needle transposal means. In this embodiment, the needle stop means comprises a slidable stop gate 142 positioned within a wall of safety receptacle 114. The resilient bias means for urging the needle 112 into the safety receptacle and for thereafter retaining the needle within the safety receptacle comprises a spring 136 surrounding a portion of the needle within the safety receptacle 114. The stop gate is slidably attached to the receptacle holding member 120. The stop gate has blocking extensions 133 which are in contact with the rearward needle portion 128 within the safety receptacle. The rearward portion 122 of the receptacle holding member is formed with a sloping trackway 135 such that relative forward movement of the receptacle holding member a predetermined distance with respect to the rearward needle portion will cause the stop gate to move outwardly to a point where the blocking extensions 133 no longer contact the rearward needle portion. At that instant, the needle becomes transposed to within the safety receptacle and is retained in the transposed position under the bias force of spring 136. The predetermined distance corresponds to movement of the catheter to the selected position as described above wherein the entire catheter is positioned substantially relatively forward of the needle.

Alternatively, the stop gate could be spring-loaded such that contact with the receptacle holding member within the safety receptacle maintains the spring in a compressed mode. In this manner, relative forward movement of the safety receptacle releases the maintaining contact such that the stop gate is moved outwardly by the spring.

Figure 8:
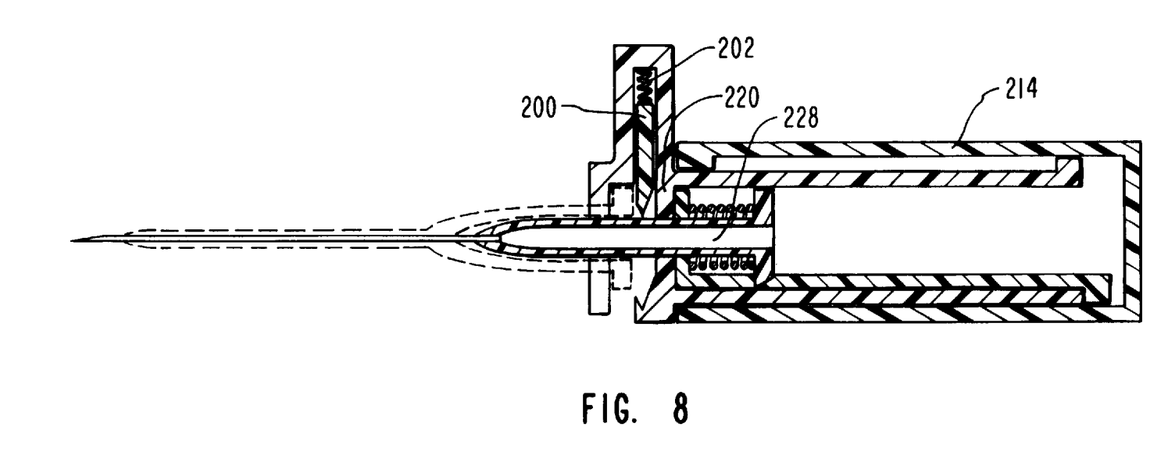
FIG. 8 is a schematic longitudinal cross-section view of a third preferred embodiment of the safety intravenous catheter insertion device of the present invention.

FIG. 8 illustrates a third preferred embodiment of the safety intravenous catheter insertion device of the present invention having self-contained coupling means and automatic needle transposal means. This longitudinal cross-section view illustrates a device similar to the device of FIG. 1. However, in the embodiment of FIG. 8, the receptacle holding member 220 is configured to substantially fully encircle the rearward needle portion 228 within the safety receptacle 214. It will be appreciated that this configuration of the receptacle holding member permits the overall length of the catheter insertion device to be shortened because, as the receptacle holding member is moved forward relative to the rearward needle portion, the substantially fully substantially encircling receptacle holding member acts as an extension of the safety receptacle. It will be further appreciated that means for locking the receptacle holding member to the safety receptacle following needle transposal must be included to ensure that the transposed needle is securely retained.

The locking means are preferably automatic to prevent a user from omitting to activate the locking means and thereby risk the receptacle holding member sliding backwardly relative to the safety receptacle and exposing the needle forward portion. Locking means of various types are known in the art. An exemplary automatic locking means is shown in FIG. 8. The locking means comprise a blocking gate 200 positioned between the catheter holding member and the receptacle holding member and biased by a spring 202 to move into a position that blocks the needle bore through the catheter holding member. Thus, it will be understood that, once needle transposal has occurred, the needle is no longer within the needle bore, and the gate will move into position to block the needle bore under the bias force of the spring. The spring retains the gate in position to block the needle bore and thereby prevents the fully substantially encircling receptacle holding member from sliding backwardly relative to the safety receptacle.

It will be appreciated that the self-contained coupling means of the present invention which require needle transposal into the safety receptacle prior to catheter separation from the device provide an advantage in an intravenous catheter insertion device whether needle transposal is effected automatically or manually. In particular, because the needle must be transposed prior to catheter separation, if the transposal means are not automatic, the user must nevertheless activate the transposal means before the catheter can be separated from the device. Thus, use of the protective needle transposal means cannot be omitted or circumvented by a user's failure to activate the transposal means because the catheter will not be separable until the needle is transposed into the safety receptacle.

Figure 9:
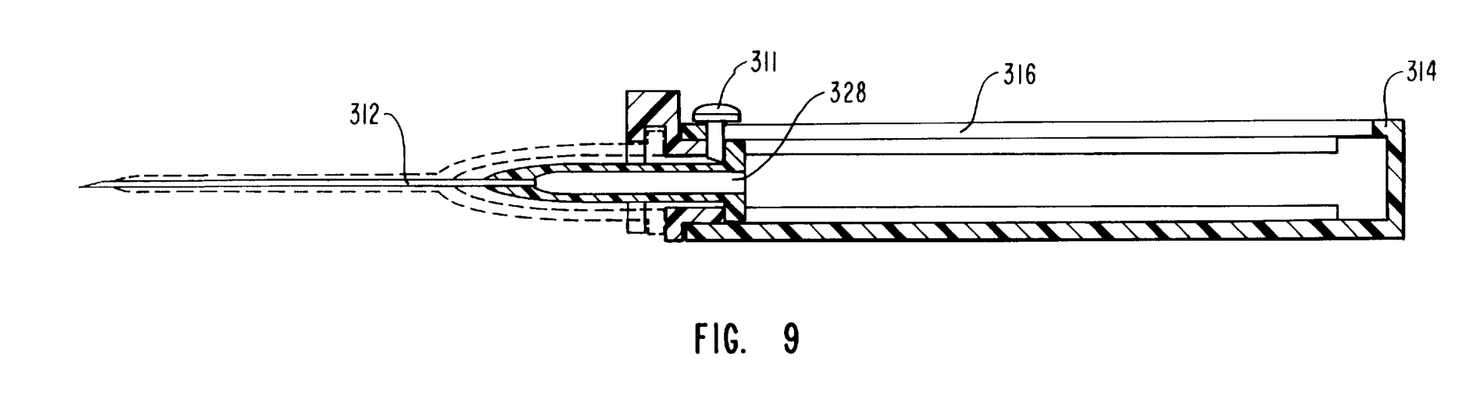
FIG. 9 is a schematic longitudinal cross-section view of a preferred embodiment of the safety intravenous catheter insertion device of the present invention having manual needle transposal means.

Accordingly, it should be understood that various known methods of manually transposing a needle into a safety receptacle could be used in an intravenous catheter insertion device in accord with the present invention. FIG. 9 illustrates a preferred embodiment of the safety intravenous catheter insertion device of the present invention having self-contained coupling means and manual needle transposal means. The selfcontained coupling means are preferably the same as those illustrated in FIG. 1. Instead of automatic needle transposal means, however, the rearward needle portion 328 is attached to a projecting knob 311 extending through a slide slot 316 formed in the safety receptacle 314. Following catheter emplacement, the projecting knob must be grasped and moved backwardly relative to the catheter to manually transpose the needle 312 into the safety receptacle.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A safety intravenous catheter insertion device for use in introducing and emplacing an intravenous catheter within a body vessel, said catheter insertion device comprising:

a needle, a safety receptacle, needle transposal means initiated within the interior of said safety receptacle by a relative positioning of a catheter with respect to said needle for transposing said needle into said safety receptacle, and self-contained coupling means for holding the catheter in place and preventing separation of the catheter from the device while said safety receptacle and said needle are withdrawn from said catheter and until the needle is transposed into the safety receptacle, wherein said catheter cannot be separated from said safety receptacle without initiating said needle transposal means.

2. A safety intravenous catheter insertion device for use in introducing and emplacing an intravenous catheter within a body vessel, said catheter insertion device comprising:

a needle, a safety receptacle, automatic needle transposal means triggered within the interior of said safety receptacle when a catheter is relatively beyond said needle for transposing said needle into said safety receptacle, and self-contained coupling means for holding the catheter in place and preventing separation of the catheter from the device while said safety receptacle and said needle are withdrawn from said catheter and until the needle is transposed into the safety receptacle.

3. A safety intravenous catheter insertion device for use in introducing and emplacing an intravenous catheter within a body vessel, said catheter insertion device comprising:

a) a needle;
b) a safety receptacle;
c) needle transposal means triggered within the interior of said safety receptacle by a relative positioning of a catheter with respect to said needle into said safety receptacle; and
d) self-contained coupling means for holding the catheter in place and preventing separaton of the catheter from the device while said safety receptacle and said needle are withdrawn from saud catheter and until the needle is transposed into the safety receptacle, said coupling means comprising a catheter holding member releasably attachable to said catheter, wherein said catheter cannot be separated from said safety receptacle without triggering said needle transposal means.

4. A safety intravenous catheter insertion device for use in introducing and emplacing an intravenous catheter within a body vessel, said catheter insertion device comprising:

a needle;
b) a safety receptacle;
c) needle transposal means triggered within the interior of said safety receptacle by a relative positioning of a catheter with respect to said needle for transposing said needle into said safety receptacle; and
d) self-contained coupling means for holding the catheter in place and preventing separation of the catheter from the device while said safety receptacle and said needle are withdrawn from said catheter and until the needle is transposed into the safety receptacle, said coupling means comprising a catheter holding member releasably attachable to said catheter and a receptacle holding member at least partially within said safety receptacle, wherein said catheter cannot be separated from said safety receptacle without triggering said needle transposal means.

5. A safety intravenous catheter insertion device for use in introducing and emplacing an intravenous catheter within a body vessel, said catheter insertion device comprising:

a) a needle;
b) a safety receptacle;
c) automatic needle transposal means triggered within the interior of said safety receptacle for transposing said needle into said safety receptacle upon positioning of the catheter from a first position to a selected position relative to said needle, said first position being where a forward needle portion extends from said safety receptacle beyond said catheter and said selected position being where the entire catheter is positioned substantially relatively beyond said needle, said automatic needle transposal means comprising needle stop means for retaining the needle in said first position and resilient bias means for urging said needle into said safety receptacle and for thereafter retaining said needle within said safety receptacle upon release of said needle stop means; and d) self-contained coupling means for holding the catheter in place and preventing separation of the catheter from the device while said safety receptacle and said needle are withdrawn from said catheter and until the needle is transposed into the safety receptacle, said coupling means comprising a catheter holding member releasably attachable to said catheter and a receptacle holding member at least partially within said safety receptacle.

6. A safety intravenous catheter insertion device as described in claim 5 wherein said resilient bias means comprises a spring surrounding a portion of the needle within said safety receptacle.

7. A safety intravenous catheter insertion device as described in claim 6 wherein said needle stop means are maintained by contact with said portion of said receptacle holding member within said safety receptacle such that positioning of the catheter in the selected position relative to said needle releases the maintaining contact between said needle stop means and said receptacle holding member.

8. A safety intravenous catheter insertion device as described in claim 7 wherein said needle stop means comprises a latch member attached to the needle within the safety receptacle, said latch member biased into a notch by pressure from contact with the receptacle holding member such that positioning of the catheter in the selected position relative to said needle releases said pressure to thereby cause said latch member to disengage from said notch.

9. A safety intravenous catheter insertion device for use in introducing and emplacing an intravenous catheter within a body vessel, said catheter insertion device comprising:

a) a safety receptacle having a forward endpiece with a needle bore therethrough;
b) a needle slidably engaged with said needle bore such that a rearward end portion of said needle is within said safety receptacle;
c) self-contained coupling means for holding the catheter in place and preventing separation of the catheter from the device while said safety receptacle and said needle are withdrawn from said catheter and until the needle is transposed into the safety receptacle, said coupling means comprising a catheter holding member releasably attachable to said catheter and a receptacle holding member at least partially within said safety receptacle, said catheter holding member having a needle bore therethrough slidably engaged with said needle, said catheter holding member being positioned adjacent to said safety receptacle endpiece such that said endpiece needle bore and said catheter holding member needle bore are aligned with each other; and
d) automatic needle transposal means triggered within the interior of said safety receptacle for transposing said needle into said safety receptacle upon positioning of the catheter from a first position to a selected position relative to said needle, said first position being where a forward needle portion extends from said safety receptacle beyond said catheter and said selected position being where the entire catheter is positioned substantially relatively beyond said needle, said automatic needle transposal means comprising needle stop means for retaining the needle in said first position and resilient bias means for urging said needle into said safety receptacle and for thereafter retaining said needle within said safety receptacle upon release of said needle stop means.

10. A safety intravenous catheter insertion device as described in claim 9 wherein said resilient bias means comprises a spring surrounding a portion of the needle within said safety receptacle and wherein said needle stop means are maintained by contact with said portion of said receptacle holding member within said safety receptacle such that positioning of the catheter in the selected position relative to said needle releases the maintaining contact between said needle stop means and said receptacle holding member.

11. A safety intravenous catheter insertion device for use in introducing and emplacing an intravenous catheter within a body vessel, said catheter insertion device comprising:

a) a safety receptacle having a forward endpiece with a needle bore therethrough;

b) a needle slidably engaged with said needle bore such that a rearward end portion of said needle is within said safety receptacle;

c) self-contained coupling means for holding the catheter in place and preventing separation of the catheter from the device while said safety receptacle and said needle are withdrawn from said catheter and until the needle is transposed into the safety receptacle, said coupling means comprising a catheter holding member releasably attachable to said catheter and a receptacle holding member at least partially within said safety receptacle, said catheter holding member having a needle bore therethrough slidably engaged with said needle, said catheter holding member being positioned adjacent to said safety receptacle endpiece such that said endpiece needle bore and said catheter holding member needle bore are aligned with each other; and d) automatic needle transposal means triggered within the interior of said safety receptacle for transposing said needle into said safety receptacle comprising needle stop means for retaining the needle in a first position where a forward needle portion extends from said safety receptacle beyond said catheter, said needle stop means maintained by contact with said portion of said receptacle holding member within said safety receptacle such that positioning of the catheter from said first position to a selected position where the entire catheter is positioned substantially relatively beyond said needle releases the maintaining contact between said needle stop means and said receptacle holding member, and resilient bias means comprising a spring surrounding a portion of the needle within said safety receptacle for urging said needle into said safety receptacle and for thereafter retaining said needle within said safety receptacle upon release of said maintaining contact between said needle stop means and said receptacle holding member.

* * * * *